United States Patent
Stiasny et al.

(10) Patent No.: US 6,420,584 B1
(45) Date of Patent: Jul. 16, 2002

(54) PROCESS FOR THE PREPARATION OF ORTHO-SUBSTITUTED ARYLMETAL COMPOUNDS AND THEIR REACTION WITH ELECTROPHILIC REAGENTS

(75) Inventors: Hans Christian Stiasny, Griesheim; Volker Reiffenrath, Rossdorf, both of (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/465,748

(22) Filed: Dec. 17, 1999

(30) Foreign Application Priority Data

Dec. 19, 1998 (DE) .......................................... 198 58 855

(51) Int. Cl.$^7$ .............................. C07F 7/08; C07F 7/10
(52) U.S. Cl. ................. 556/415; 556/419; 556/214; 556/402; 556/403; 556/52; 556/121; 260/665 R
(58) Field of Search ..................... 260/665 R; 556/415, 556/419, 214, 402, 403, 52, 121

(56) References Cited

U.S. PATENT DOCUMENTS

| | | | | |
|---|---|---|---|---|
| 5,626,798 A | * | 5/1997 | Schwindeman et al. | 260/665 R |
| 5,663,398 A | * | 9/1997 | Schwindeman et al. | 260/665 R |
| 6,261,482 B1 | * | 7/2001 | Wietelmann et al. ... | 260/665 R |

FOREIGN PATENT DOCUMENTS

WO  WO89/02425  3/1989  ........... C07C/25/18

* cited by examiner

*Primary Examiner*—Paul F. Shaver
(74) *Attorney, Agent, or Firm*—Millen, White, Zelano & Branigan, P.C.

(57) ABSTRACT

Ortho-substituted arylmetal compounds are prepared by deprotonation of aromatics which have a hydrogen atom in the ortho position relative to at least one halogen atom, one trifluoromethoxy group, one dialkylamino group, one nitrile group, one alkoxy group or one dialkylamido group. The arylmetal compounds can then be reacted with electrophilic reagents. Deprotonation of the aromatics is carried out using alkyl- or arylmetal compounds or metal hydrides in the presence of a catalytic amount of a secondary metal amide.

19 Claims, No Drawings

PROCESS FOR THE PREPARATION OF ORTHO-SUBSTITUTED ARYLMETAL COMPOUNDS AND THEIR REACTION WITH ELECTROPHILIC REAGENTS

The invention relates to a process for the preparation of ortho-substituted arylmetal compounds by deprotonation of aromatics which have a hydrogen atom in the ortho position relative to at least one halogen atom, one trifluoromethoxy group, one dialkylamino group, one nitrilo group, one alkoxy group or one dialkylamido group, and their reaction with electrophilic reagents, characterized in that the deprotonation of the aromatics is carried out using alkyl- or arylmetal compounds or metal hydrides in the presence of a catalytic amount of a secondary metal amide.

Substituted aromatics are useful intermediates for the synthesis of high-value-added end products or are themselves such end products for the electronics industry, such as, for example, liquid crystals, for crop protection, such as, for example, pesticides or for the preparation of pharmaceutically high-active substances, such as, for example, dopamine receptor blockers, antiemetics or antipsychotics.

This is true in particular of aromatics which are substituted in the ortho position relative to a halogen atom, a trifluoromethoxy group, a dialkylamino group, a nitrile group, an alkoxy group or a dialkylamido group.

A variety of methods for the preparation of such compounds are described in the literature.

Thus, for example, the metallation, described by D. L. Ladd in J. Org. Chem. 46, 203 (1981), of 1,4-difluorobenzene with butyllithium at <−65° C. gives 1-lithium-2,5-difluorobenzene, which is reacted at the same (low) temperature with trimethyl borate to give dimethyl 2,5-difluorobenzeneboronate (Scheme 1).

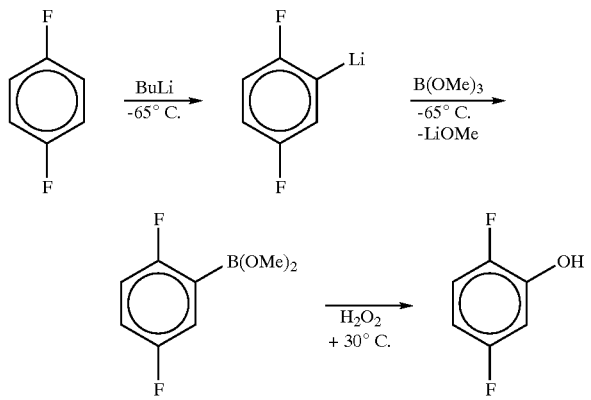

The boronate is oxidized with hydrogen peroxide to give the corresponding phenol.

This reaction sequence is also described in WO 89/2425 for the preparation of 2,3-difluorophenol, the reaction temperatures being unchanged and the reaction conditions being changed only slightly (Scheme 2).

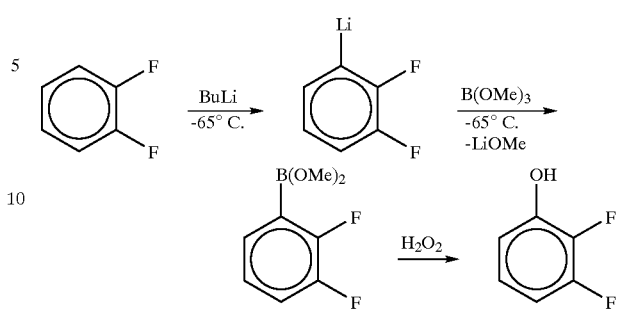

WO 89/2425 further describes the preparation of liquid-crystalline 2,3- or 2',3'-difluoro-p-terphenylene starting from 1,2-difluorobenzene. WO 89/8629 describes the synthesis of other liquid-crystalline compounds which have a 2,3-difluoro-1,4-phenylene group. In the processes described therein, the 1,2-difluorobenzene or 1-substituted 2,3-difluorobenzene is deprotonated using a strong base, normally using n-butyllithium, and the resulting 2,3-difluorophenyllithium compound is reacted with an electrophilic reagent.

The reason for the low reaction temperatures is the poor stability of the ortho-haloarylmetal compounds. For example, 2,3-difluorophenyllithium derivatives eliminate lithium fluoride above −50° C., forming 1-fluoro-2,3-benzene derivatives, which further react in an uncontrolled manner to give unknown secondary products. At −50° C. the rate of the decomposition reaction of the 2,3-difluorophenyllithium derivative is still slight, but proceeds in an explosive manner at −25° C. (critical temperature −22.5° C.), the 2,3-difluorophenyllithium derivatives decomposing suddenly.

Analogously to the ortho-fluoroarylmetal compounds, other ortho-haloarylmetal compounds are also obtainable using ortho position hydrogen with the help of a base (e.g. Houben-Weyl, Methoden der organischen Chemie, [Methods of Organic Chemistry], vol. 13/1, 122–123, Stuttgart 1970).

However, other ortho-haloarylmetal compounds usually have an even lower stability than the ortho-fluoroarylmetal compounds, meaning that the decomposition reactions occur at considerably lower temperatures. For example, from Bull. Soc. Chim. France 1986 No. 6, 925–929, it is known that chloroaryl compounds metallated in the ortho position readily eliminate chloride in an exothermic reaction, as a result of which arynes are formed, which give rise to the formation of undesired byproducts.

According to DE 42 19 281, it is also possible to replace those hydrogen atoms of an aromatic which are in the ortho position relative to a trifluoromethoxy group. Furthermore, deprotonations in the ortho position to other groups such as, for example, alkoxy groups, cyano groups, amines and amides have been described (S. Patai (ed.) The Chemistry of the functional groups, Vol. 4, John Wiley & Sons 1987, pages 59–67). In the case of these groups too, it is usually necessary to maintain low temperatures in order to avoid secondary reactions.

Very low temperatures are required particularly when the aromatic to be deprotonated contains reactive groups, such as ester or cyano groups, which would react with the arylmetal compound already formed or with the base used at relatively high temperatures.

Many of said aromatics which, because of their reactive groups, can also react as electrophilic reagents, such as, for example, benzonitriles, are therefore preferably deprotonated using a lithium amide, which is prepared from secondary amines, in order to avoid an addition of alkyllithium compounds to the electrophilic groups (e.g. J. Org. Chem. 47, 2681, 1982). However, for industrial processes deprotonations using such lithium-amides are unsuitable because of the high costs of the parent amine.

The very low temperatures which must generally be observed for the sensitive ortho-substituted arylmetal compounds have proven to be a disadvantage particularly when aromatics with only a very slightly acidic hydrogen atom are to be deprotonated. Such aromatics frequently require very long reaction times, but produce only poor yields, or often cannot be deprotonated at all at low temperatures, whilst at higher temperatures secondary reactions occur. Higher rates of deprotonation and thus also better yields of arylmetal compound can frequently not be achieved for the processes of the prior art if low temperatures are maintained.

An object of the present invention is to provide a process for the preparation of ortho-substituted arylmetal compounds and their reaction with electrophilic reagents and in particular a process for the preparation of ortho-haloarylmetal compounds and their reaction with electrophilic reagents, which does not have the described disadvantages of the processes to date and can be carried out at favorable cost on an industrial scale.

Upon further study of the specification and appended claims, further objects and advantages of this invention will become apparent to those skilled in the art.

It has now been found that the preparation of arylmetal compounds by deprotonation of aromatics which have a hydrogen atom in the ortho position relative to a halogen atom, a trifluoromethoxy group, a dialkylamino group, a nitrile group, an alkoxy group or a dialkylamido group can be carried out safely and with high yield if the corresponding aromatics are treated with alkyl- or arylmetal compounds or metal hydrides in the presence of a catalytic amount of a secondary metal amide. The ortho-substituted arylmetal compounds formed can be reacted with electrophilic reagents in the usual manner.

In the process according to the invention, catalytic amounts of a secondary amine are converted into the corresponding metal amide using an alkyl- or arylmetal compound or a metal hydride. Following deprotonation of the respective aromatic by this metal amide, the amine reformed during the reaction is again converted into the metal amide by alkylmetal or arylmetal compound present or a metal hydride. Surprisingly, the use of catalytic amounts of the secondary amine increases the rate of deprotonation and the yield of arylmetal compound, although metal amides generally have lower basicity than, for example, alkyllithium compounds.

According to the process of the invention, it is surprisingly possible to prepare lithiated aromatics, which can be used as useful intermediates, for example for liquid crystals, auxiliaries, plant-protection compositions and pharmaceuticals, in a simple and cost-effective manner in high yields. The use of only catalytic amounts of the secondary amine reduces the costs and simplifies work-up of the reaction mixtures since only small amounts of the amine have to be removed and, if necessary, disposed of.

The invention thus provides a process for the preparation of ortho-substituted arylmetal compounds by deprotonation of aromatics which have a hydrogen atom in the ortho position relative to at least one halogen atom, one trifluoromethoxy group, one dialkylamino group, one nitrilo group, one alkoxy group or one dialkylamido group, wherein the alkyl and alkoxy portions have preferably up to 15 carbon atoms, especially 1 to 3 carbon atoms, and their reaction with electrophilic reagents, characterized in that the deprotonation of the aromatics is carried out using alkyl- or arylmetal compounds or metal hydrides in the presence of a catalytic amount of a secondary metal amide.

A preferred subject of the invention is a process for the preparation of ortho-substituted arylmetal compounds and their reaction with corresponding electrophilic reagents to give the compounds of the formula I,

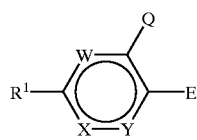

I where

Q is F, Cl, CN, OCF$_3$, CONR$_2$, NR$_2$ or OR,

R is alkyl having from 1 to 7 carbon atoms,

R$^1$ is H, F, Cl, Br, CN, alkyl, alkenyl, alkoxy, alkenyloxy, each having up to 18 carbon atoms, or a mesogenic group, W, X and Y in each case independently of one another are N, CH, CCN, CCl or CF, and

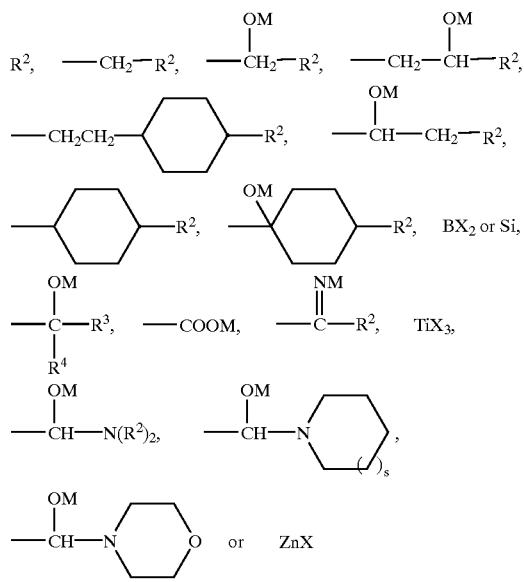

in which

R$^2$ is alkyl, alkoxy, alkenyl, alkenyloxy having up to 15 carbon atoms, or a mesogenic radical, M is Li, K or Na, s is 0 or 1, BX$_2$ is a group of the formula —B(OR$^3$)(OR$^4$) or a trioxatriborinone radical of the formula

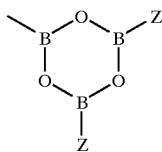

in which Z is

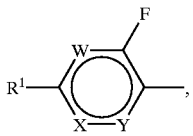

$R^3$ and $R^4$ are H, alkyl, alkenyl or cycloalkyl each having up to 10 carbon atoms or taken together an alkylenediyl group of the formula —$(CH_2)_n$— or —$CH_2CHR^5$—$CH_2$—, in which n is 2, 3 or 4, and $R^5$ is alkyl, alkoxy or alkenyl having up to 18 carbon atoms or a mesogenic radical, and SI is a trihydrocarbylsilyl group of the formula —$Si(R^6)_3$ in which $R^6$ is in each case independently of one another an aliphatic, cycloaliphatic, araliphatic or aromatic radical having up to 12 C atoms, preferably up to 7 C atoms, $TiX_3$ is a radical of the formula $TiBr_3$, $TiCl_3$ or $Ti(OR_3)_3$ and ZnX is a radical of the formula ZnBr, ZnCl, $ZnR^3$ or $ZnOR^3$ characterized in that the deprotonation of the aromatics is carried out using alkyl- or arylmetal compounds or metal hydrides in the presence of a catalytic amount of a secondary metal amide.

In particular, the invention provides processes in which $R^1$, $R^2$, and/or $R^5$ is a mesogenic group of the formula II, where $$R^0\text{—}A^1\text{—}Z^1\text{—}(A^2\text{—}Z^2)_m\text{—} \qquad II$$

$R^0$ is F, CN, an alkyl or alkenyl radical having up to 15 carbon atoms which is unsubstituted or monosubstituted by CN, halogen or $CF_3$, where in these radicals one or more $CH_2$ groups can also be replaced in each case independently of one another by —S—, —O—, —CO—, —CO—O—, —O—CO— or —O—CO—O— such that S— and/or O— atoms are not linked directly to one another, $Z^1$ and $Z^2$ in each case independently of one another are —$CH_2CH_2$—, —C≡C—, —$CH_2$—, —$OCH_2$—, —CO—O—, —O—CO—, —CH=N—, —N=CH—, —$CH_2S$—, —$SCH_2$—, a single bond or an alkylene group having from 3 to 6 carbon atoms in which a $CH_2$ group can also be replaced by —O—, —CO—O—, —O—CO—, —CHhalogen— or —CHCN—, and $A^1$ and $A^2$ in each case independently of one another are
a) a trans-1,4-cyclohexylene radical in which one or more nonadjacent $CH_2$ groups can also be replaced by —O— and/or —S—,
b) a 1,4-phenylene radical in which one or two CH groups can also be replaced by N.
c) a radical from the group consisting of 1,3-cyclobutylene, 1,3-bicyclo(1,1,1)-pentylene, 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) can be substituted by CN or halogen such as F, and m is 0, 1 or 2.

The ortho-haloaryl derivatives prepared by the process according to the invention include mono-, di-, tri- and tetrahalophenyl derivatives, and pentahalophenyl derivatives. Halo refers to fluoro, chloro, bromo and iodo, preferably fluoro.

A particularly preferred embodiment of the invention is one where the arylmetal compounds obtained by metallation are reacted with a metal halide such as, for example, $ZnCl_2$ or $ZnBr_2$, or other metal compounds, such as, for example, $Ti(OR^3)_4$, preferably titanium tetraisopropoxide, titanium tetramethoxide, titanium tetraethoxide or titanium tetra-n-propoxide. The compounds obtained by this transmetallation are generally more thermally stable than the starting materials and can likewise be reacted with electrophilic reagents.

In addition, 2-halopyridin-3-yl derivatives can also be prepared by the process according to the invention. Whether other substituents are present in the aromatic ring in addition to the halogen substituents is unimportant for carrying out the process according to the invention. Other substituents which may be mentioned are, for example, alkyl, alkenyl or alkoxy groups, chlorine and bromine or mesogenic groups. In addition, the halogenated aromatic rings can also be constituents of condensed ring systems, such as, for example, of naphthalenes, di- and tetrahydronaphthalenes or of 2,3,4,5-tetrahydro-1H-3-benzazepine derivatives.

For the sake of simplicity, in the text below Phe is a 1,4-phenylene group, in which one or two CH groups can also be replaced by N, and the 1,4-phenylene group can also be substituted by one or two halogen atoms.

ArF is a fluorinated 1,4-phenylene group of the formula

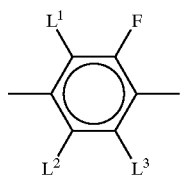

where $L^1$, $L^2$ and $L^3$ in each case independently of one another are H or F.

Cyc is a trans-1,4-cyclohexylene radical, in which one or more nonadjacent $CH_2$— groups can also be replaced by —O—, and which can be substituted by halo, preferably F, or CN.

E is a group which has been introduced by the reaction according to the invention.

Preferred electrophilic reagents are the following compounds of the formula IIIa to IIIq:

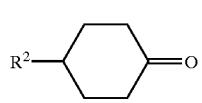
IIIa $R^2$—CHO  IIIb

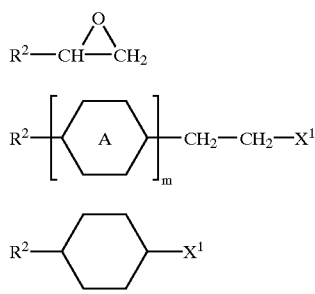  IIIc

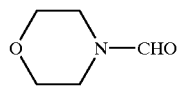  IIId

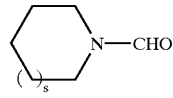  IIIe

R²—CH₂—X¹   IIIf

R³—CO—R⁴   IIIg (R²)₂N—CHO   IIIh

CO₂   IIIi

Halogens   IIIj

Ti(OR³)₃   IIIk

ZnCl₂   IIIl

IIIp

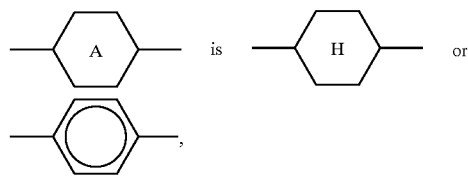

IIIq

Si—L   IIIm

B(OR³)₂(OR⁴)   IIIn1 in which $R^2$ is alkyl, alkoxy, alkenyl, alkenyloxy having from 1 to 15 carbon atoms or a mesogenic group corresponding to the formula II,

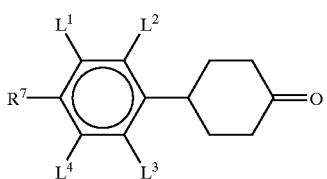

m is 1 or 2, and $X^1$ is Cl, Br, iodine, a toluene- or benzenesulfonic acid group or a perfluoroalkyl sulfonic acid group. Halogens preferably mean F, Cl, Br, I, in particular Br or I. $R^3$ and S have the meaning given above.

Silylation reagents are the compounds of the formula IIIm SI—L, in which SI has the given meaning and L is a leaving group, in particular compounds of the formulae IIIm1 to IIIm8:

(CH₃)₃Si—Cl   IIIm1

(CH₃)SiBr   IIIm2

(CH₃)₃Si_I_   IIIm3

(CH₃)₃SiOSO₂CF₃   IIIm4

(CH₃)₂(tert-C₄H₉)SiCl   IIIm5

(C₆H₅)₂(tert-C₄H₉)SiCl   IIIm6

(C₂H₅)₃SiCl   IIIm7

(I—C₃H₇)₃SiCl   IIIm8

To prepare the compounds of the formula I in which E is $B(OR^3)(OR^4)$, trialkyl borates of the formula IIIn1 $B(OR^3)_2(OR^4)$ are preferably suitable.

Particular preference is given to using the electrophilic reagents of the formulae IIIa1 to IIIn1 for the process according to the invention:

IIIa1

IIIa2

IIIa3

IIIa4

IIIa5

IIIa6

IIIa7

IIIa8

IIIa9

-continued

IIIa10: R⁷-[phenyl(L¹,L²,L³,L⁴)]-CH₂CH₂-[cyclohexyl]=O

IIIa11: R⁷-[phenyl(L¹,L²,L³,L⁴)]-CH=CH-[cyclohexyl]=O

IIId1: R⁷-[cyclohexyl]-CH₂—CH₂—X¹

IIId2: R⁷-[phenyl]-CH₂—CH₂—X¹

IIId3: R⁷-[cyclohexyl]-[phenyl(L¹,L²)]-CH₂CH₂—X¹

IIIe1: R⁷-[cyclohexyl]-X¹

IIIe2: R⁷-[cyclohexyl]-[cyclohexyl]-X¹

IIIe3: R⁷-[cyclohexyl]-CH₂—CH₂-[cyclohexyl]-X¹

IIIh1: (CH₃)N—CHO

IIIp1: morpholine-N—CHO

IIIq1: piperidine-N—CHO

IIIm1: (H₃C)₃SiCl

IIIm5: (H₃C)₂(tert-C₄H₉)SiCl

IIIn1: B(OR³)₂(OR⁴)

in which R⁷ is preferably an alkyl, alkoxy, alkenyl or alkenyloxy radical having up to 12 carbon atoms, and L¹, L², L³ and L⁴ are H or F, and X¹ has the meaning given above.

Further preferred electrophilic reagents for the process according to the invention are the ketones of the formula IIIo IIIo: R⁸—CO—R⁹ in which

R⁸ and R⁹ are independently of one another an alkyl or alkenyl radical having up to 15 carbon atoms and which is unsubstituted or monosubstituted by CN, halogen or CF₃, where in these radicals one or more CH₂ groups in each case independently of one another can be replaced by —S—, —O—, A, —CO—, —CO—O—, —O—CO— or —O—CO—O such that —S— and/or —O— atoms are not linked directly to one another.

A is in each case independently of one another
  (a) a trans-1,4-cyclohexylene radical in which one or more nonadjacent CH₂ groups can also be replaced by —O— and/or —S—.
  (b) A 1,4-phenylene radical in which one or two CH groups can also be replaced by N.
  (c) A radical from the group consisting of 1,3-cyclobutylene, 1,3-bicyclo(1,1,1)pentylene, 1,4-cyclohexenylene, 1,4-bicyclo(2,2,2)octylene and piperidine-1,4-diyl, where the radicals (a), (b) and (c) can be mono- or polysubstituted by R⁸, R⁹, CN or halogen.

Particularly preferably, the process according to the invention is used to metallate the compounds of the formulae IV1 to IV10.

IV1: R¹-[phenyl]-Q with L¹ substituent

IV2: R¹-[phenyl(L¹)]-Q with L¹ substituent

IV3: R¹-[phenyl(L³,L⁴)]-[phenyl(L¹,L²)]-Q¹

IV4: R¹-[cyclohexyl]-[phenyl(L¹,L²)]-Q¹

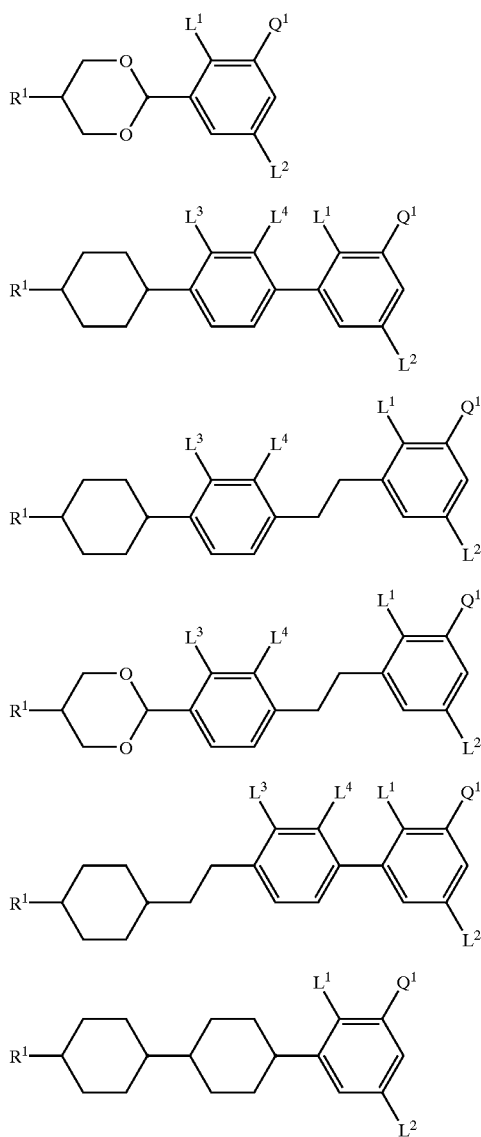

in which Q and $R^1$ are as defined above, and $L^1$, $L^2$, $L^3$ and $L^4$ independently of one another are H or F. $Q^1$ is F or Cl, in particular F.

Preferably, only one of the radicals $L^1$ and $L^2$ is H and the other is F.

The compounds of the formula I prepared by the process according to the invention include those of the formulae Ia to Ii:

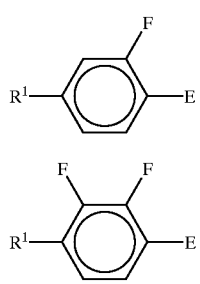

Of these, the compounds of the formulae Ia, Ib, Id and Ig are particularly preferred. In said compounds of the formulae Ia to Ii, $R^1$ is preferably H, alkyl or alkoxy having in each case from 1 to 12 carbon atoms, or a mesogenic radical, particular preference being given according to the process of the invention to compounds of the formula Ib in which $R^1$ is H or alkoxy having from 1 to 12, in particular from 2 to 4, carbon atoms.

The compounds of the formulae Ib, Ie, If and Ig are particularly suitable as intermediates for the preparation of liquid crystals having a 2,3-difluoro-1,4-phenylene or 2,3-difluoro-1,4-phenylenoxy structural unit. The compounds of the formula I which have a mesogenic radical of the formula II include the preferred compounds of the formulae I1 to I13:

$R^0$—$A^1$—ArF—E    I1

$R^0$—$A^1$—$Z^1$—ArF—E    I2

| | |
|---|---|
| R⁰—A¹—A²—ArF—E | I3 |
| R⁰—A¹—A²—Z²—ArF—E | I4 |
| R⁰—A¹—Z¹—A²—ArF—E | I5 |
| R⁰—A¹—Z¹—A²—Z²—ArF—E | I6 |
| R⁰—A¹—A²—A²—ArF—E | I7 |
| R⁰—A¹—Z¹—A²—A²—ArF—E | I8 |
| R⁰—A¹—A²—Z²—A²—ArF—E | I9 |
| R⁰—A¹—A²—A²—Z²—ArF—E | I10 |
| R⁰—A¹—Z¹—A²—Z²—A²—ArF—E | I11 |
| R⁰—A¹—Z¹—A²—A²—Z²—ArF—E | I12 |
| R⁰—A¹—A²—Z²—A²—Z²—ArF—E | I13 |

Of these, the compounds of the formulae I1, I2, I3, I4 and I7 are particularly preferred.

Of the compounds of the formula I1, those of the formulae I1a to I1c are particularly preferred.

| | |
|---|---|
| Alkyl-Phe-ArF—E | I1a |
| Alkyl-Cyc-ArF—E | I1b |
| Alkoxy-Phe-ArF—E | I1c |

Of the compounds of the formula I2, those of the formulae I2a to I2i are particularly preferred.

| | |
|---|---|
| Alkyl-Phe-CH₂CH₂—ArF—E | I2a |
| Alkyl-Phe-CH₂O—ArF—E | I2b |
| Alkyl-Phe-C≡C—ArF—E | I2c |
| Alkoxy-Phe-C≡C—ArF—E | I2d |
| Alkoxy-Phe-CH₂O—ArF—E | I2e |
| Alkoxy-Phe-CH₂CH₂—ArF—E | I2f |
| Alkyl-Cyc-CH₂CH₂—ArF—E | I2g |
| Alkyl-Cyc-CH₂O—ArF—E | I2h |
| Alkyl-Cyc-C≡C—ArF—E | I2i |

The following group of compounds includes the particularly preferred compounds I14 to I28, which can be prepared by the process according to the invention.

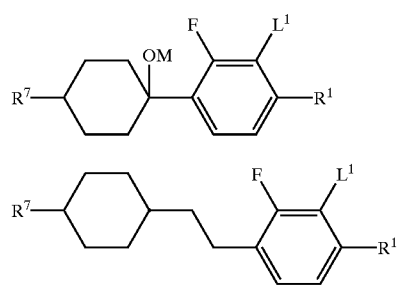

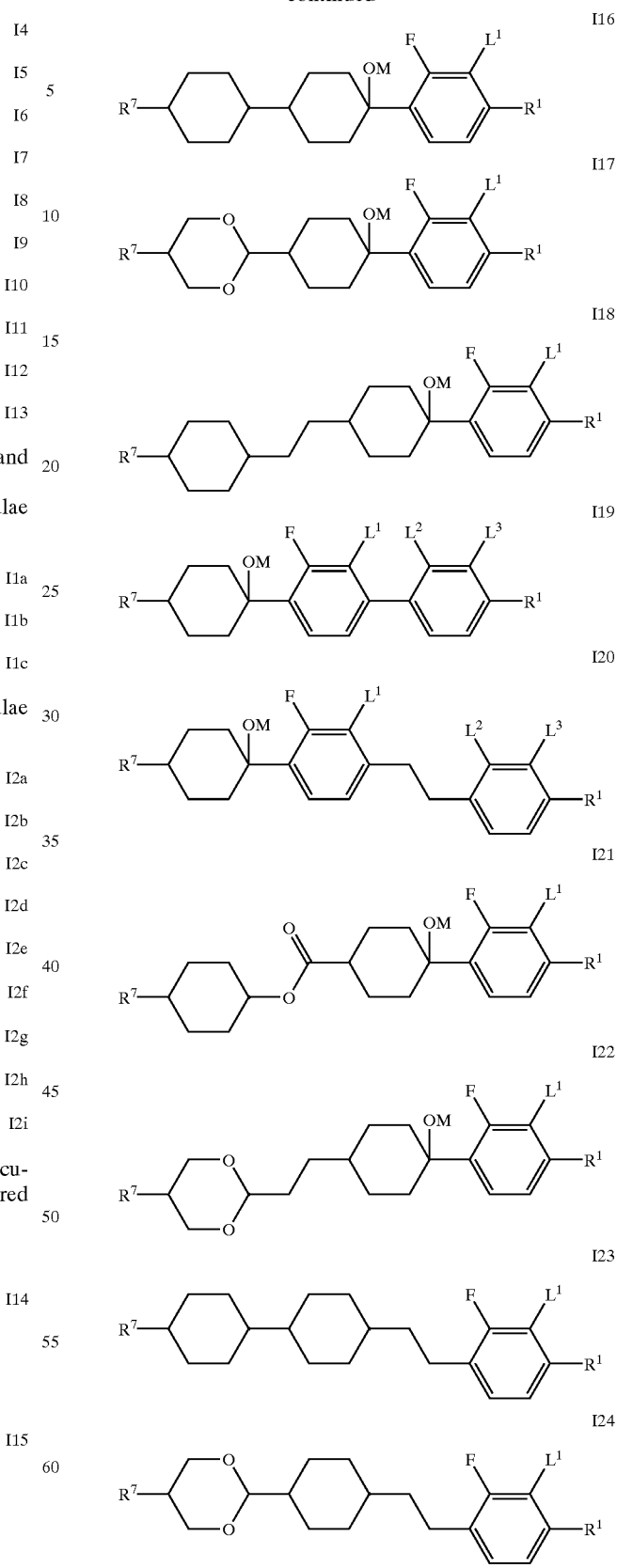

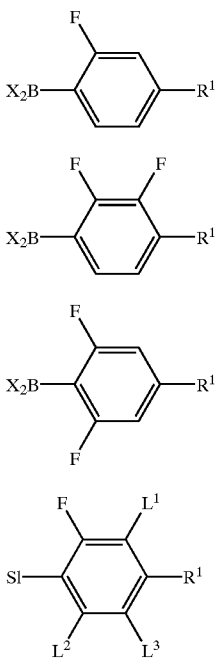

in which $R^1$, $R^7$, $BX_2$, M and SI assume the meaning given above. $L^1$, $L^2$ and $L^3$ independently of one another are H or F.

The secondary metal amide used in catalytic amount is obtained by reaction with the corresponding alkyl- or aryl-metal compounds or a metal hydride preferably from the secondary amines of the formula V or VI:

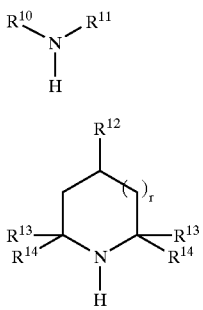

in which
$R^{10}$ and $R^{11}$ are alkyl or cycloalkyl having from 1 to 15 carbon atoms, aryl or trimethylsilyl or triethylsilyl, $R^{12}$ is H, OH, alkoxy or cycloalkoxy having from 1 to 15 carbon atoms, trimethylsilyloxy or triethylsilyloxy and r is 0, 1 or 2, preferably 1. $R^{13}$ and $R^{14}$ are H, alkyl having from 1 to 5 carbon atoms or aryl, preferably H, or alkyl having from 1 to 3 carbon atoms, particularly preferably H, methyl, ethyl or n-propyl.

$R^{10}$ and $R^{11}$ are preferably alkyl having from 1 to 10 carbon atoms, cycloalkyl or trimethylsilyl, in particular methyl, ethyl, n-propyl, n-butyl, isopropyl, 2-butyl (=1-methylpropyl), isobutyl (=2-methylpropyl), tert-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl or trimethylsilyl.

$R^{12}$ is preferably H, OH, alkoxy having from 1 to 3 carbon atoms or trimethylsilyloxy.

Preference is given to compounds of the formula V, in which $R^{10}$ and $R^{11}$ are the same. Compounds of the formula VI in which $R^{13}$ and $R^{14}$ are the same are preferable.

In the preferred compounds of the formulae above and below, $R^1$ and $R^2$ independently of one another are alkyl groups having preferably from 1 to 10 carbon atoms, alkoxy, alkenyl groups or alkenyloxy groups having, preferably, in each case from 1 to 10 carbon atoms.

Particularly preferred alkyl groups are n-hexyl, n-pentyl, n-butyl, i-butyl, propyl, i-propyl, methyl and ethyl, in particular methyl; particularly preferred alkoxy groups are n-hexoxy, n-pentoxy, n-butoxy, i-butoxy, n-propoxy, i-propoxy, methoxy and ethoxy, in particular methoxy; particularly preferred alkenyl groups are hexenyl, pentenyl, butenyl and allyl.

In the preferred compounds of the formulae above and below, the alkyl radicals in which, in addition, a $CH_2$ group (alkoxy or oxaalkyl) can be replaced by an O atom, can be straight-chain or branched. They preferably have 2, 3, 4, 5, 6, 7, 8, 9 or 10 carbon atoms and are accordingly preferably ethyl, propyl, butyl, pentyl, hexyl, heptyl, octyl, nonyl, decyl, propoxy, ethoxy, butoxy, pentoxy, hexoxy, heptoxy, octoxy, nonoxy or decoxy, and also undecyl, dodecyl, undecoxy, dodecoxy, 2-oxapropyl (=2-methoxypentyl), 2-, 3- or 4-oxapentyl, 2-, 3-, 4- or 5-oxahexyl, 2-, 3-, 4-, 5- or 6-oxaheptyl.

$A^1$ and $A^2$ are preferably Cyc or Phe. In the compounds of the formulae above and below, Phe is preferably a 1,4-phenylene group (Ph), a 1,4-phenylene group (PheX) mono- or disubstituted by F or CN, a pyrimidine-2,5-diyl group (Pyr), a pyridine-2,5-diyl group (Pyn), a pyrazine-3, 6-diyl group or a pyridazine-2,5-diyl group, particularly preferably Ph, PheX, Pyr or Pyn. The compounds prepared by the process according to the invention preferably contain no more than one 1,4-phenylene group in which one or two CH groups have been replaced by N. Cyc is preferably a 1,4-cyclohexylene group. However, particular preference is given to compounds of the formula I in which one of the groups $A^1$ and $A^2$ is a 1,4-cyclohexylene group substituted by CN or F in the 1- or 4-position, and the nitrile group or the fluorine atom is in an axial position, i.e. the group $A^1$ or $A^2$ has the following structure:

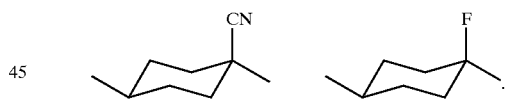

Particular preference is given to compounds of the formula I and of the above subformulae which contain a —Phe-Phe— grouping. —Phe-Phe— is preferably —Ph-Ph—, Pyr-Phe or Ph-Pyn. Particular preference is given to the groups

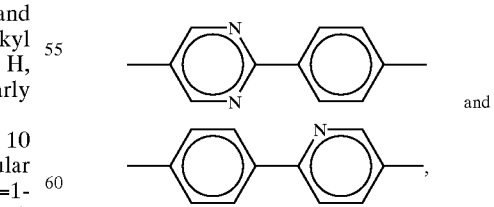

also 4,4'-biphenylyl which is unsubstituted or mono- or polysubstituted by fluorine.

Particular preference is given to compounds of the formula I and of the subformulae below which contain a 2,3-difluoro-1,4-phenylene group.

The groups $Z^1$ and $Z^2$ are in each case independently of one another preferably a single bond, secondarily preferably —C≡C— or —CH$_2$CH$_2$— groups. Particularly preferred are compounds of the formulae I in which a group $Z^1$ is —CH$_2$CH$_2$—. Compounds of the formulae above and below having branched wing groups $R^1$ can be of importance. Branched groups of this type generally contain not more than two chain branches. $R^1$ is preferably a straight-chain group or a branched group with not more than one chain branch.

Preferred branched radicals are isopropyl, 2-butyl (=1-methylpropyl), isobutyl (=2-methylpropyl), tert-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl.

The radical $R^1$ can also be an optically active organic radical containing an asymmetric carbon atom. The asymmetric carbon atom is then preferably linked to two differently substituted carbon atoms, an H atom and a substituent chosen from the group consisting of fluorine, alkyl or alkoxy having in each case from 1 to 5 carbon atoms, and CN.

wherein Q, $R^1$, W, X and Y are as defined above, are known or are prepared by methods known per se, as described in the literature (e.g. in standard works such as Houben-Weyl, Methoden der organischen Chemie, [Methods of Organic Chemistry], Georg-Thieme-Verlag, Stuttgart), under reaction conditions which are known and suitable for said reactions. Use can also be made here of variants which are known per se but which are not mentioned here in greater detail.

The metal alkoxides produced during the reaction of arylmetal compounds with electrophilic reagents such as ketones, aldehydes or oxiranes are worked up under aqueous conditions to give the corresponding alcohols, which can be further processed by known methods. It is likewise possible to further process the metal alkoxides directly by known methods.

Other possible uses for the compounds prepared by the process according to the invention are described, for example, in EP 440082, incorporated herein by reference.

The following schemes give preferred further processing possibilities:

Scheme 3

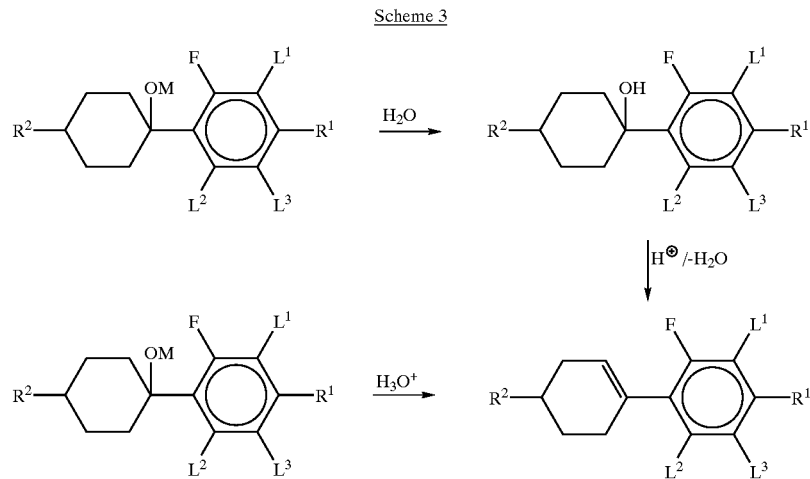

Of the compounds of the formulae above and below, preference is given to those in which at least one of the radicals present therein has one of the preferred meanings given.

The compounds of the formula IV required as starting materials,

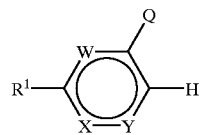

IV

Scheme 4

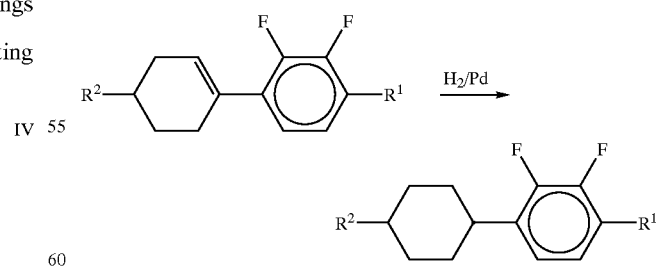

Scheme 5

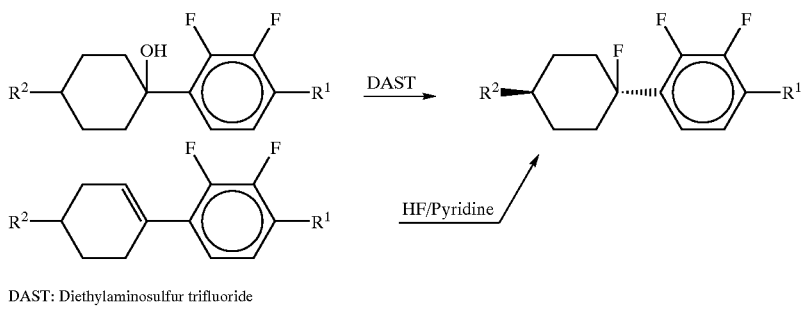

DAST: Diethylaminosulfur trifluoride

Preference is given to the process according to the invention for the preparation of ortho-substituted aryllithium compounds, arylpotassium compounds or arylsodium compounds and their reaction with electrophilic reagents, in particular for the preparation of ortho-substituted aryllithium compounds and their reaction with electrophilic reagents.

The reaction procedure for the process according to the invention is simple, with firstly the ortho-substituted arylmetal compounds preferably being prepared by reacting the corresponding Aromatics and a catalytic amount of a secondary amine with alkyl- or arylmetal compounds or metal hydrides at temperatures of from −100° C. to +100° C., preferably from −80° C. to +40° C., in particular at −35° C. to 0° C. The ortho-substituted arylmetal compounds formed are then reacted with an electrophilic reagent, preferably at the same or a higher temperature.

Preferably, the molar ratio of aromatic to be deprotonated to alkyl- or arylmetal compound or to metal hydride is from 1:1 to 1:5, preferably from 1:1 to 1:2, in particular from 1:1 to 1:1.2. A catalytic amount of the amine preferably means from 25 0.1 to 90 mol %, in particular from 0.2 to 30 mol % and very particularly preferably from 1 to 15 mol %, based on the compound to be deprotonated. The ortho-substituted arylmetal compound formed is preferably reacted with a n excess of electrophilic reagent. The molar ratio of this arylmetal compound to the electrophilic reagent is particularly preferably from 1:1 to 1:10, preferably from 1:1 to 1:2.

The starting materials, i.e. aromatic to be metallated, alkyl- or arylmetal compound or metal hydride and also the electrophilic reagent and the secondary amine are preferably dissolved or suspended in inert solvents which are conventionally suitable for reactions with strong bases, such as, for example, ethers such as diethyl ether, tetrahydrofuran or methyl tert-butyl ether, hydrocarbons such as pentane, hexane, heptane, benzene, toluene, xylene or cyclohexane or mixtures of said solvents. These solvents can also be admixed with cosolvents, such as, for example, hexamethylphosphoramide (HMPT), tetramethylethylenediamine (TMEDA), dimethylpropyleneurea (DMPU) or crown ethers, such as 18-crown-6. The amount of solvent is unimportant, it generally being possible to use from 100 to 1000 g of solvent per mole of the compounds to be dissolved.

The alkyl- or arylmetal compounds used are preferably the lithium compounds normally customary in organic chemistry (e.g. House: Modern Synthetic Reactions, 2nd Ed., Benjamin 1972, 547). Particularly suitable alkyl- and aryllithium compounds are n-butyllithium, sec-butyllithium, tert-butyllithium, methyllithium, ethyllithium, n-propyllithium, i-propyllithium, hexyllithium or phenyllithium. It is, however, also possible to use all other known alkyl- and aryllithium compounds which are not specifically mentioned here. Alkyllithium compounds are preferred. It is, however, also possible to use other alkyl- and arylmetal compounds such as, for example, phenylsodium or phenylpotassium. Although alkyl- and aryllithium compounds are preferred, it is likewise possible to use, for example, alkylpotassium compounds, which are preferably prepared in situ from potassium tert-butoxide and alkyllithium (e.g. Angew. Chem. Int. Ed. Engl. 12, 508 1973). The additional stoichiometric or substoichiometric use of potassium tert-butoxide frequently results in a further increase in the rate of the reaction and in the yield. Potassium tert-butoxide is preferably used in a molar ratio to the aromatic to be deprotonated of from 1:100 to 1:1, in particular from 1:50 to 1:1.

Suitable metal hydrides are preferably potassium hydride and sodium hydride.

If the intention is to prepare substituted aryllithium compounds by the process according to the invention, preference is given to using alkyllithium compounds for the deprotonation. If the intention is to prepare arylpotassium compounds, preference is given to using alkyllithium compounds in the presence of potassium tert-butoxide or potassium hydride for the deprotonation. If the intention is to prepare arylsodium compounds, preference is given to using sodium hydride.

For the process according to the invention, catalytic amounts of a secondary amine, preferably diisopropylamine, piperidine, pyrrolidine or 2,2,6,6-tetramethylpiperidine, 2,2,6,6-tetramethyl-4-methoxypiperidine, 2,2,6,6-tetramethyl-4-silyloxypiperidine, 2,2,6,6-tetramethylpiperidinol, 2,2,5,5-tetramethylpyrrolidine or bis(trimethylsilyl)amine, are used, which amine is converted into the corresponding metal amide by adding an alkyl- or arylmetal compound. Following deprotonation of an ortho-substituted aromatic by the metal amide, the amine reformed during the reaction is again converted into the metal amide by alkyl- or arylmetal compound which is present. The amine can be added either to the metal compound or else to the aromatic to be deprotonated. It is preferably added to the aromatic to be deprotonated.

The use of catalytic amounts of the amine increases the yield of ortho-substituted arylmetal compound and the rate of deprotonation.

For the process according to the invention for the preparation of arylmetal compounds by deprotonation, preference is given to using those aromatics which have a hydrogen atom in the ortho position relative to a fluorine or a chlorine atom or a trifluoromethoxy group.

It is also possible to carry out the process according to the invention for the metallation of aromatics in a continuous-flow reactor. This is also true for the subsequent reaction with an electrophilic reagent. This enables the ortho-substituted arylmetal compound formed to be reacted continuously with a suitable electrophilic reagent.

The process according to the invention can be carried out in an analogous manner to processes described, for example, in EP 440 082 B1 and DE 42 01 308 C1. For this, preferably the electrophilic reagent, the aromatic and the secondary amine are initially introduced and the alkyl- or arylmetal compound or the metal hydride is added at room temperature. The intermediate ortho-substituted arylmetal compounds are immediately scavenged in situ by the electrophilic reagent in question, thus avoiding an accumulation of the unstable component. The addition of a catalytic amount of a secondary amine frequently results in an increase in yield compared with the processes described therein.

Suitable electrophilic reagents are preferably said compounds of the formulae IIIa to IIIn1, preferably cyclohexanones such as 4-alkyl-, alkoxy-, alkenyl-, alkenyloxy- or cycloalkylcyclohexanone or 4-arylcyclo-hexanone, or else simple aliphatic or unsaturated ketones such as acetone, butanone, 2-pentanone, methyl vinyl ketone, diethyl ketone, 2-hexanone, 3-hexanone, methyl isobutyl ketone, ethyl isopropyl ketone, diisopropyl ketone, ethyl isobutyl ketone, isobutyl isopropyl ketone, 2-heptanone, 3-heptanone, 4-heptanone, diisobutyl ketone, methyl vinyl ketone, mesityl oxide, acetonylacetone, benzylideneacetone, dibenzalacetone, pinacolone, ethyl tert-butyl ketone, phenylacetone, acetophenone, benzophenone, menthone, phorone, ketoglutaric ester, levulinic ester, diacetone acrylamide, isomethadone, normethadone, pseudoionone, ionone, dipipanone, norpipanone, teprenone, hygrine, cuscohygrine, 3-indolylacetate, phenadoxone, nabumetone or solanone, n-alkyl halides having from 1 to 16 carbon atoms, in particular n-alkyl bromides and iodides, such as, for example, methyl, ethyl, propyl, butyl, pentyl, hexyl, heptyl, octyl or nonyl bromide or methyl, ethyl, propyl, butyl, pentyl, hexyl, heptyl, octyl or nonyl iodide, n-alkanals having from 2 to 16 carbon atoms, in particular acetaldehyde, propionaldehyde, butyraldehyde, pentanal, hexanal, heptanal, octanal or nonanal, oxiranes such as, for example, oxirane, 2-methyloxirane, 2-ethyloxirane, 2-propyloxirane, 2-butyloxirane, 2-pentyloxirane, 2-hexyloxirane or 2-heptyloxirane.

Suitable silylating agents are the compounds of the formulae IIIm, preferably trialkylsilyl halides, where the alkyl groups are straight-chain or branched and have from 1 to 8 carbon atoms, in particular the compounds of the formulae IIIm1 to IIIm8.

Suitable trialkyl borates are usually compounds of the formula IIIn1 $B(OR^3)_2(OR^4)$, preferably $B(OR^3)_3$, where $R^3$ is preferably methyl, ethyl, propyl, butyl or isopropyl, in particular methyl or isopropyl.

In a preferred embodiment of the process according to the invention, the deprotonation of a halo- or trifluoromethoxy aromatic is achieved by firstly adding to the solution of the aromatic preferably from 1 to 50 mol %, in particular from 2 to 20 mol %, of the secondary amine which can be converted into a metal amide by deprotonation, and introducing this mixture into a continuous-flow reactor in a defined mass or volume stream. The base used is preferably a solution of an alkyllithium compound, which is preferably introduced into the continuous-flow reactor in a mass or volume stream which contains a molar ratio of the base to the aromatic of from 1:1 to 1:2, preferably from 1:1 to 1:1.2.

In the process, an intermediate formed from the added amine is the corresponding lithium amide, which deprotonates the halo- or trimethoxy aromatic and is then converted into the amide again by further alkyllithium. After a reaction zone which is sufficient for complete lithiation of the aromatic, a solution of the electrophilic reagent is introduced into the continuous-flow reactor in a mass or volume stream which contains a molar ratio of the electrophilic reagent to the metallated aromatic of from 1:1 to 1:0.5, preferably from 1:1 to 1:0.8. After passing through a further reaction zone in which the electrophilic reagent is reacted with the arylmetal compound, the product stream leaves the continuous-flow reactor.

Work-up of the reaction mixture and isolation of the products is carried out in the customary manner, e.g. by pouring the reaction mixture, which, if ketones, aldehydes or epoxides are used as electrophilic reagent, comprises the corresponding metal alkoxides as product, onto water and/or ice or dilute acid and, following removal of the aqueous phase, isolating the products in the form of the respective alcohols by distillation or crystallization.

If amides are used as electrophilic reagents, the corresponding metallated hemiaminals initially form which, after protonation, fragment into the respective aldehydes.

The entire disclosure of all applications, patents and publications, cited above and below, and of corresponding German application No. 198 58, 855.0 filed Dec. 19, 1998 is hereby incorporated by reference.

EXAMPLES

The examples below serve to illustrate the invention without limiting it. Above and below, percentages are percentages by weight. All temperatures are given in degrees Celsius. M.p.=melting point. Unless stated otherwise, from 1.0 to 1.2 equivalents (based on aromatic used) of the electrophilic reagent in each case were used in the examples.

"Customary work-up" means that water is added if necessary, the mixture is extracted with methylene chloride, diethyl ether or toluene, the organic phase is separated off, dried and evaporated, and the product is purified by distillation under reduced pressure or crystallization and/or chromatography.

The following abbreviations are used:

| | |
|---|---|
| THF | tetrahydrofuran |
| KOtBu | potassium tert-butoxide |
| RT | room temperature |
| MTBE | methyl tert-butyl ether |

Example 1

1.1 kg/h of a 1M solution of 2,3-difluorophenetole containing 10 mol % of 2,2,6,6-tetramethylpiperidine were introduced into a continuous-flow reactor and mixed with 0.4 kg/h of a 2.5M solution of hexyllithium in hexane at −35° C. After the mixture had passed through the reaction zone, 0.28 kg/h of a 4.7M solution of benzaldehyde in THF were mixed in. After the reaction had finished, the product was collected and worked up in the customary manner, giving 2,3-difluoro-4-ethoxy-α-phenylbenzyl alcohol. The conversion based on the starting compound was 97%.

Example 2

2,3-Difluoroethoxybenzene was mixed with n-hexyllithium in a tubular reactor at −30° C. and, after a

Example 3

2,3-Difluoroethoxybenzene and 10 mol % of 2,2,6,6-tetramethyl-4-piperidinole were stirred with n-hexyllithium at about −65°0 C. for 15 min and then reacted with benzaldehyde. The conversion was >99%.

Example 4

2,3-Difluorotoluene and 10 mol % of 2,2,6,6-tetramethylpiperidine were mixed with n-hexyllithium in a tubular reactor at −30° C. and, after a residence time of about 15 min, reacted with benzaldehyde. The conversion was about 96%.

Example 5

2,3-Difluorotoluene was stirred with n-hexyllithium at about −65° C. for 1 hour, and then reacted with 4-(4-ethylcyclohexyl)cyclohexanone. After isolation and the elimination of water, the alkene was purified by crystallization. The addition of 10 mol % of 2,2,6,6-tetramethylpiperidine to the aromatic increased the yield from 72 to 76%.

Example 6

1,2-Difluorobenzene and 10 mol % of 2,2,6,6-tetramethylpiperidine were stirred with n-hexyllithium at about −65° C. for 15 min and then reacted with benzaldehyde. The conversion was about 95%.

Example 7

3-(4-Propylcyclohexyl)fluorobenzene was stirred with n-hexyllithium at about −70° C. for 1 h and reacted with trimethylsilyl chloride. While the addition of 10 mol % of 2,2,6,6-tetramethylpiperidine achieved a conversion of only 12%, this increased to 92% upon the addition of 50 mol % of 2,2,6,6-tetramethylpiperidine and 50 mol % of KOtBu.

The compounds below are obtained in an analogous manner by the process according to the invention using the corresponding precursors.

Examples 8–11

| | $R^O$ | $(A-Z)_n$ | $R^2$ | L |
|---|---|---|---|---|
| (8) | n-Propyl | — | n-Propyl | F |
| (9) | n-Pentyl | — | n-Propyl | F |
| (10) | n-Pentyloxy | — | n-Pentyloxy | F |
| (11) | CH=CH$_2$ | — | CH=CH$_2$ | H |

Examples 12–28

| | $R^O$ | $(A-Z)_n$ | $L^1$ | $L^2$ |
|---|---|---|---|---|
| (12) | n-Propyl | — | F | H |
| (13) | n-Pentyl | — | F | H |
| (14) | n-Pentyloxy | — | F | H |
| (15) | CH=CH$_2$ | — | H | F |
| (16) | OCH$_2$CH=CH$_2$ | — | H | F |
| (17) | n-Propyl | — | F | H |
| (18) | n-Propoxy | — | F | H |
| (19) | CH$_2$CH=CH$_2$ | — | F | H |
| (20) | n-Butyl | — | F | H |
| (21) | n-Butyloxy | — | F | H |
| (22) | n-Pentyl | — | H | F |
| (23) | Ethyl | — | F | H |
| (24) | CH=CH$_2$ | — | H | F |
| (25) | Methyl | — | H | H |
| (26) | OCH$_2$CH=CH$_2$ | — | F | H |
| (27) | n-Butyl | cyclohexyl | H | F |
| (28) | Methoxy | cyclohexyl | H | F |

Examples 29–34

(29) 4-n-Propyl-2,6-difluorobenzeneboronic anhydride
(30) 4-(4-Propylcyclohexyl)-2,3-difluorobenzeneboronic anhydride
(31) 4-Propyl-2,3-difluorobenzeneboronic anhydride
(32) 4-(4-Ethylphenyl)-2,3-difluorobenzeneboronic anhydride
(33) 4-(2-(4-(4-Propylcyclohexyl)cyclohexyl)ethyl)-2,3-difluorobenzeneboronic anhydride
(34) 4-Ethoxy-2,3-difluorophenylboronic anhydride

Example 35

3,5-Difluoro(4-propylcyclohexyl)benzene and 2 mol % of 2,2,6,6-tetramethylpiperidine were mixed with n-hexyllithium in a tubular reactor at −50° C. and, after a residence time of about 10 min, reacted with N-formylpiperidine. The conversion was >98%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the preparation of an ortho-substituted arylmetal compound comprising:

deprotonating an aromatic having a hydrogen atom in the ortho position relative to at least one halogen atom, one

--- residence time of about 15 min, reacted with benzaldehyde. The addition of 10 mol % of 2,2,6,6-tetramethylpiperidine to the aromatic increased the conversion from about 86% to 99%.

trifluoromethoxy group, one dialkylamino group, one nitrilo group, one alkoxy group or one dialkylamido group, wherein deprotonation is carried out using one or more alkyl metal compounds, arylmetal compounds, or metal hydrides in the presence of a catalytic amount of a secondary metal amide.

2. A process comprising reacting an ortho-substituted arylmetal compound with an electrophilic reagent, wherein said ortho-substituted arylmetal compound was prepared by:

deprotonating an aromatic having a hydrogen atom in the ortho position relative to at least one halogen atom, one trifluoromethoxy group, one dialkylamino group, one nitrilo group, one alkoxy group or one dialkylamido group, wherein deprotonation is carried out using one or more alkyl metal compounds, arylmetal compounds, or metal hydrides in the presence of a catalytic amount of a secondary metal amide.

3. A process according to claim 1, wherein the ortho-substituent of the arylmetal compound is a halogen.

4. A process according to claim 1, wherein said ortho-substituted arylmetal compound is an ortho-substituted aryl-lithium compound, an ortho-substituted arylpotassium compound or an ortho-substituted arylsodium compound.

5. A process according to claim 2, wherein the reaction with the electrophilic reagent yields a compound of the formula I,

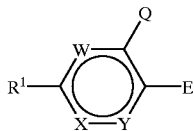

where

Q is F, Cl, CN, OCF$_3$, CONR$_2$, NR$_2$ or OR,

R is alkyl having from 1 to 7 carbon atoms,

R$^1$ is H, F, Cl, Br, CN, alkyl, alkenyl, alkoxy, alkenyloxy, each having up to 18 carbon atoms, or a mesogenic group, W, X and Y in each case independently of one another are N, CH, CCN, CCl or CF, and E is

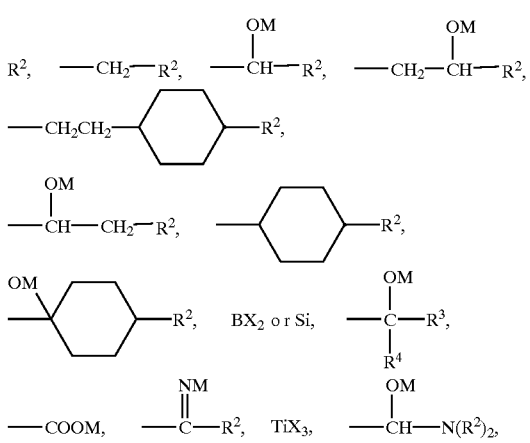

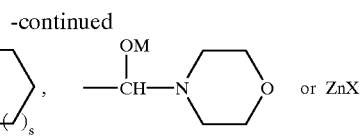

in which

R$^2$ is alkyl, alkoxy, alkenyl, or alkenyloxy each having from 1 to 15 carbon atoms, or a mesogenic radical, M is Li, K or Na, s is 0 or 1, BX$_2$ is a group of the formula —B(OR$^3$)(OR$^4$) or is a trioxatriborinone radical of the formula

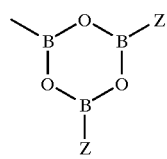

in which Z is

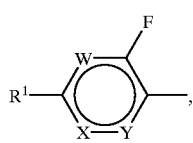

R$^3$ and R$^4$ are each independently H, alkyl, alkenyl or cycloalkyl each having up to 10 carbon atoms or taken together are an alkylenediyl group of the formula —(CH$_2$)$_n$— or —CH$_2$CHR$^5$—CH$_2$—, in which n is 2, 3 or 4, and R$^5$ is alkyl, alkoxy or alkenyl having up to 18 carbon atoms or a mesogenic radical, SI is a trihydrocarbylsilyl group of the formula —Si(R$^6$)$_3$ in which R$^6$ is in each case independently of one another an aliphatic, cycloaliphatic, araliphatic or aromatic radical having up to 12 carbon atoms, TiX$_3$ is a radical of the formula TiBr$_3$, TiCl$_3$ or Ti(OR$_3$)$_3$, and ZnX is a radical of the formula ZnBr, ZnCl, ZnR$^3$ or ZnOR$^3$.

6. A process according to claim 5, wherein R$^1$, R$^2$ and/or R$^5$ is a mesogenic group of formula II,

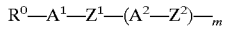

R$^0$ is F, CN, an alkyl or alkenyl radical having up to 15 carbon atoms which is unsubstituted or monosubstituted by CN, halogen or CF$_3$, where in these radicals one or more CH$_2$ groups can be replaced in each case independently of one another by —S—, —O—, —CO—, —CO—O—, —O—CO— or —O—CO—O— such that S— and/or O— atoms are not linked directly to one another, Z$^1$ and Z$^2$ in each case independently of one another are —CH$_2$CH$_2$—, —C≡C—, —CH$_2$O—, —OCH$_2$—, —CO—O—, —O—CO—, —CH=N—, —N=CH—, —CH$_2$S—, —SCH$_2$—, a single bond or an alkylene group having from 3 to 6 carbon atoms, in which, in addition, a CH$_2$ group can also be replaced by —O—, —CO—O—, —O—CO—, —CHhalogen-or —CHCN—, $A^1$ and $A^2$ in each case independently of one another are
- a) a trans-1,4-cyclohexylene radical in which one or more nonadjacent CH$_2$ groups can in each case also be replaced by —O— and/or —S—,
- b) a 1,4-phenylene radical in which, in addition, one or two CH groups can in each case be replaced by N,
- c) a radical from the group consisting of 1,3-cyclobutylene, 1,3-bicyclo(1,1,1)-pentylene, 1,4-cyclohexenylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) can be substituted by CN or F, and m is 0, 1 or 2.

7. A process according to claim 1, wherein said secondary metal amide is obtained during deprotonation from a secondary amine of formula V or VI:

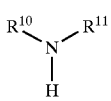    V

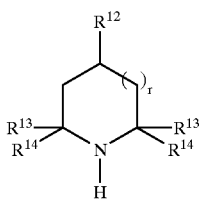    VI in which
- $R^{10}$ and $R^{11}$ are each independently alkyl or cycloalkyl having from 1 to 15 carbon atoms, aryl or trimethylsilyl or triethylsilyl,
- $R^{12}$ is H, OH, alkoxy or cycloalkoxy having from 1 to 15 carbon atoms, trimethylsilyloxy or triethylsilyloxy, and
- r is 0, 1 or 2, and
- $R^{13}$ and $R^{14}$ are each independently H, alkyl having from 1 to 5 carbon atoms or aryl.

8. A process according to claim 2, wherein said secondary metal amide is obtained during deprontenation from a secondary amine are of formula V or VI:

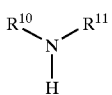    V

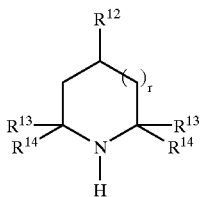    VI in which
- $R^{10}$ and $R^{11}$ are each independently alkyl or cycloalkyl having from 1 to 15 carbon atoms, aryl or trimethylsilyl or triethylsilyl,
- $R^{12}$ is H, OH, alkoxy or cycloalkoxy having from 1 to 15 carbon atoms, trimethylsilyloxy or triethylsilyloxy, and r is 0, 1 or 2, and $R^{13}$ and $R^{14}$ are each independently H, alkyl having from 1 to 5 carbon atoms or aryl.

9. A process according to claim 1, wherein alkyl lithium compounds, aryllithium compounds, potassium hydride or sodium hydride are used for deprotonation.

10. A process according to claim 2, wherein alkyl lithium compounds, aryllithium compounds, potassium hydride or sodium hydride are used for deprotonation.

11. A process according to claim 1, deprotonation is carried out in the presence of potassium tert-butoxide.

12. A process according to claim 2, deprotonation is carried out in the presence of potassium tert-butoxide.

13. A process according to claim 1, wherein deprotonation is performed at −80° C. to +40° C.

14. A process according to claim 2, wherein deprotonation is performed at −80° C. to +40° C.

15. A process according to claim 2, wherein said electrophilic reagent is of the formula IIIa to IIIq:

    IIIa

    IIIb $R^2$—CHO

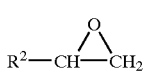    IIIc

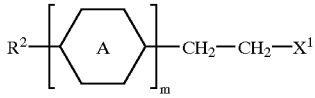    IIId

    IIIe $R^2$—CH$_2$—X$^1$    IIIf $R^3$—CO—R$^4$    IIIg $(R^2)_2$N—CHO    IIIh CO$_2$    IIIi Halogens    IIIj Ti(OR$^3$)$_3$    IIIk ZnCl$_2$    IIIl

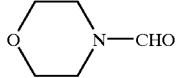    IIIp

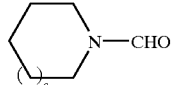    IIIq in which
- $R^2$ is alkyl having from 1 to 15 carbon atoms or a mesogenic group

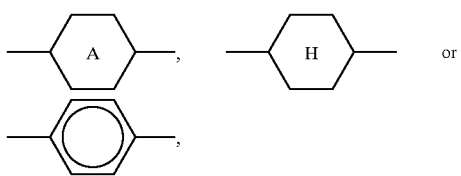

m is 1 or 2, $X^1$ is Cl, Br, iodine, a toluene- or benzenesulfonic acid group or a perfluoroalkyl sulfonic acid group, $R^3$ and $R^4$ are each independently H, alkyl, alkenyl or cycloalkyl each having up to 10 carbon atoms or taken together are an alkylenediyl group of the formula —(CH$_2$)$_n$— or —CH$_2$CHR$^5$—CH$_2$—, in which n is 2, 3 or 4, and $R^5$ is alkyl, alkoxy or alkenyl having up to 18 carbon atoms or a mesogenic radical, and s is 0 or 1.

16. A process according to claim 2, wherein said electrophilic reagent is of the formula IIIm1 to IIIm8:

| | |
|---|---|
| (CH$_3$)$_3$Si—Cl | IIIm1 |
| (CH$_3$)SiBr | IIIm2 |
| (CH$_3$)$_3$SiI | IIIm3 |
| (CH$_3$)$_3$SiOSO$_2$CF$_3$ | IIIm4 |
| (CH$_3$)$_2$(tert-C$_4$H$_9$)SiCl | IIIm5 |
| (C$_6$H$_5$)$_2$(tert-C$_4$H$_9$)SiCl | IIIm6 |
| (C$_2$H$_5$)$_3$SiCl | IIIm7 |
| (I—C$_3$H$_7$)$_3$SiCl | IIIm8. |

17. A process according to claim 2, wherein said electrophilic reagent is of the formula B(OR$^3$)$_2$(OR$^4$) wherein $R^3$ and $R^4$ are each independently H, alkyl, alkenyl or cycloalkyl each having up to 10 carbon atoms or taken together are an alkylenediyl group of the formula —(CH$_2$)$_n$— or —CH$_2$CHR$^5$—CH$_2$—, in which n is 2, 3 or 4, and $R^5$ is alkyl, alkoxy or alkenyl having up to 18 carbon atoms or a mesogenic radical.

18. A process according to claim 1, wherein n-butyllithium, sec-butyllithium, tert-butyllithium, methyllithium, ethyllithium, n-propyllithium, i-propyllithium, hexyllithium, phenyllithium, potassium hydride and sodium hydride are used for deprotonation.

19. A process according to claim 5, wherein the aromatic starting material is a compound of the formula IV

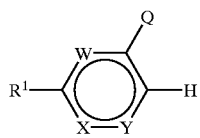

IV wherein

Q is F, Cl, CN, OCF$_3$, CONR$_2$, NR$_2$ or OR,

R is alkyl having from 1 to 7 carbon atoms, $R^1$ is H, F, Cl, Br, CN, alkyl, alkenyl, alkoxy, alkenyloxy, each having up to 18 carbon atoms, or a mesogenic group, and W, X and Y in each case independently of one another are N, CH, CCN, CCl or CF.

* * * * *

UNITED STATES PATENT AND TRADEMARK OFFICE
CERTIFICATE OF CORRECTION

PATENT NO.    : 6,420,584 B1
DATED         : July 16, 2002
INVENTOR(S)   : Appel et al.

It is certified that error appears in the above-identified patent and that said Letters Patent is hereby corrected as shown below:

<u>Title page,</u>
Item [73], should read -- Geesthacht --

Signed and Sealed this

Twenty-second Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,420,584 B1
DATED : July 16, 2002
INVENTOR(S) : Hans Christian Stiasny et al.

It is certified that error appears in the above-identified patent and that said Letters Patent is hereby corrected as shown below:

This certificate supersedes Certificate of Correction issued July 22, 2003, the number was erroneously mentioned and should be vacated since no Certficate of Correction was granted.

Signed and Sealed this

Twenty-third Day of March, 2004

JON W. DUDAS
*Acting Director of the United States Patent and Trademark Office*